United States Patent
Evans et al.

(10) Patent No.: US 8,742,147 B2
(45) Date of Patent: Jun. 3, 2014

(54) PROCESS FOR IMPROVING THE SELECTIVITY OF AN EO CATALYST

(75) Inventors: Wayne Errol Evans, Houston, TX (US); Marek Matusz, Houston, TX (US); Paul Michael McAllister, Houston, TX (US)

(73) Assignee: Shell Oil Company, Houston, TX (US)

( * ) Notice: Subject to any disclaimer, the term of this patent is extended or adjusted under 35 U.S.C. 154(b) by 88 days.

(21) Appl. No.: 13/310,273

(22) Filed: Dec. 2, 2011

(65) Prior Publication Data

US 2012/0149926 A1 Jun. 14, 2012

Related U.S. Application Data (60) Provisional application No. 61/420,846, filed on Dec. 8, 2010.

(51) Int. Cl.
| | |
|---|---|
| C07D 301/03 | (2006.01) |
| C07C 43/00 | (2006.01) |
| C07C 31/18 | (2006.01) |
| C07C 29/03 | (2006.01) |

(52) U.S. Cl.
USPC ............ 549/536; 568/672; 568/852; 568/867

(58) Field of Classification Search
USPC ............................ 549/536; 568/867, 852, 672
See application file for complete search history.

(56) References Cited

U.S. PATENT DOCUMENTS

| | | | |
|---|---|---|---|
| 4,761,394 A | 8/1988 | Lauritzen .................. | 502/348 |
| 4,766,105 A | 8/1988 | Lauritzen .................. | 502/216 |
| 4,822,900 A | 4/1989 | Hayden .................... | 549/534 |
| 4,845,296 A | 7/1989 | Ahmed et al. ............. | 564/477 |
| 4,874,879 A | 10/1989 | Lauritzen et al. ......... | 549/536 |
| 5,155,242 A | 10/1992 | Shankar et al. ........... | 549/534 |
| 5,380,697 A | 1/1995 | Matusz et al. ............. | 502/348 |
| 5,739,075 A | 4/1998 | Matusz ..................... | 502/302 |
| 5,801,259 A | 9/1998 | Kowaleski ................ | 549/536 |
| 6,040,467 A | 3/2000 | Papavassiliou et al. ..... | 549/534 |
| 6,080,897 A | 6/2000 | Kawabe .................... | 568/858 |
| 6,368,998 B1 | 4/2002 | Lockemeyer .............. | 502/347 |
| 6,372,925 B1 | 4/2002 | Evans et al. ............... | 549/536 |
| 6,717,001 B2 | 4/2004 | Evans et al. ............... | 549/536 |
| 7,102,022 B2 | 9/2006 | Evans et al. ............... | 549/536 |
| 7,193,094 B2 | 3/2007 | Chipman et al. .......... | 549/536 |

(Continued)

FOREIGN PATENT DOCUMENTS

| | | | | |
|---|---|---|---|---|
| EP | 003642 | 8/1979 | .......... | C07D 301/10 |
| EP | 352850 | 1/1990 | .......... | C07D 301/10 |

(Continued)

OTHER PUBLICATIONS

Kirk-Othmer Encyclopedia of Chemical Technology. 3rd edition, vol. 9, 1980. pp. 445-447.

(Continued)

*Primary Examiner* — Taylor Victor Oh (57) ABSTRACT

The present invention relates to a process for improving the overall selectivity of an EO process for converting ethylene to ethylene oxide utilizing a highly selective EO silver catalyst containing a rhenium promoter wherein following normal operation a chloride strip of the chloride on the surface of the catalyst is conducted in order to remove a portion of the chlorides on the surface of the catalyst. The chloride strip involves the addition of certain saturated hydrocarbons to the feed. Following the chloride strip, the catalyst is optionally re-optimized.

19 Claims, 1 Drawing Sheet

(56) References Cited

U.S. PATENT DOCUMENTS

| | | | |
|---|---|---|---|
| 7,235,677 B2 | 6/2007 | Chipman et al. | 549/536 |
| 7,348,444 B2 | 3/2008 | Evans et al. | 549/534 |
| 7,485,597 B2 | 2/2009 | Lockemeyer et al. | 502/216 |
| 7,657,331 B2 | 2/2010 | Chipman et al. | 700/28 |
| 2004/0049061 A1 | 3/2004 | Lockemeyer et al. | 549/536 |
| 2007/0129557 A1 | 6/2007 | Chipman et al. | 549/535 |
| 2009/0069583 A1 | 3/2009 | Rizkalla et al. | 549/536 |
| 2009/0234144 A1 | 9/2009 | Bos et al. | 549/534 |
| 2009/0281339 A1 | 11/2009 | Matusz et al. | 549/523 |
| 2009/0281345 A1 | 11/2009 | Matusz | 558/260 |

FOREIGN PATENT DOCUMENTS

| | | | | |
|---|---|---|---|---|
| EP | 1532125 | 1/2004 | | C07D 301/10 |
| EP | 1458698 | 4/2005 | | C07D 301/10 |
| EP | 2155708 | 11/2008 | | C07D 301/10 |
| GB | 1544081 | 4/1979 | | |
| WO | WO2004078737 | 1/2004 | | C07D 301/10 |
| WO | WO2004078736 | 9/2004 | | C07D 301/10 |
| WO | WO2007095453 | 8/2007 | | B01J 21/04 |

OTHER PUBLICATIONS

B.E.T. (Brunaner, Emmett and Teller) method as described in Journal of the American Chemical Society 60 (1938) pp. 309-316.

Rebsdat et al., "Ethylene Oxide", Ullmann's Encyclopedia of Industrial Chemistry, Mar. 2001, vol. 13, pp. 548-572. Wiley-VCH Verlag GmbH & Co. KGaA, Weinheim, Germany, XP55025249, ISBN: 978-3-52-730673-2.

PCT International Preliminary Report on Patentability date Jun. 12, 2013, Ref. No. TH3716-PCT, Application No. PCT/US2011/063511 filed Dec. 6, 2011.

PROCESS FOR IMPROVING THE SELECTIVITY OF AN EO CATALYST

This application claims the benefit of U.S. Provisional Application 61/420,846 filed Dec. 8, 2010, which is herein incorporated by reference.

FIELD OF THE INVENTION

The invention relates to a process for the operation of an ethylene epoxidation process which employs a silver-based highly selective epoxidation catalyst. The invention also relates to a process for the production of ethylene oxide, a 1,2-diol, a 1,2-diol ether, a 1,2-carbonate, or an alkanolamine.

BACKGROUND OF THE INVENTION

In olefin epoxidation an olefin is reacted with oxygen to form an olefin epoxide, using a catalyst comprising a silver component, usually with one or more further elements deposited therewith on a support. The olefin oxide may be reacted with water, an alcohol or an amine to form a 1,2-diol, a 1,2-diol ether or an alkanolamine. Thus, 1,2-diols, 1,2-diol ethers and alkanolamines may be produced in a multi-step process comprising olefin epoxidation and converting the formed olefin oxide with water, an alcohol or an amine.

The performance of the epoxidation process may be assessed on the basis of the selectivity, the catalyst's activity, and stability of operation. The selectivity is the molar fraction of the converted olefin yielding the desired olefin oxide. Modern silver-based epoxidation catalysts are highly selective towards olefin oxide production. When using the modern catalysts in the epoxidation of ethylene the selectivity towards ethylene oxide can reach values above 85 mole-%. An example of such highly selective catalysts is a catalyst comprising silver and a rhenium promoter, for example U.S. Pat. No. 4,761,394, U.S. Pat. No. 4,766,105 and US 2009/0281345A1.

For decades much research has been devoted to improving the activity, the selectivity, and the lifetime of the catalysts, and to find process conditions which enable full exploitation of the catalyst performance. A reaction modifier, for example an organic halide, may be added to the feed in an epoxidation process for increasing the selectivity of a highly selective catalyst (see for example EP-A-352850, U.S. Pat. No. 4,761, 394 and U.S. Pat. No. 4,766,105, which are herein incorporated by reference). The reaction modifier suppresses the undesirable oxidation of olefin or olefin oxide to carbon dioxide and water, relative to the desired formation of olefin oxide. EP-A-352850 teaches that there is an optimum in the selectivity as a function of the quantity of organic halide in the feed, at a constant oxygen conversion level and given set of reaction conditions.

Many process improvements are known that can improve selectivity. For example, it is well known that low $CO_2$ levels are useful in improving the selectivity of high selectivity catalysts. See, e.g., U.S. Pat. No. 7,235,677; U.S. Pat. No. 7,193,094; US Pub. Pat. App. 2007/0129557; WO 2004/078736; WO 2004/078737; and EP 2,155,708. These patents also disclose that water concentration in the reactor feed should be maintained at a level of at most 0.35 mole percent, preferably less than 0.2 mole percent. Other patents disclose control of the chloride moderator to maintain good activity. See, e.g., U.S. Pat. No. 7,657,331; EP 1,458,698; and U.S. Pub. Pat. App. 2009/0069583. Still further, there are many other patents dealing with EO process operation and means to improve the performance of the catalyst in the process. See, e.g., U.S. Pat. Nos. 7,485,597, 7,102,022, 6,717,001, 7,348, 444, and U.S. Pub. Pat. App. 2009/0234144.

All catalysts must first be started up in a manner to establish a good selectivity operation. U.S. Pat. No. 7,102,022 relates to the start-up of an epoxidation process wherein a highly selective catalyst is employed. In this patent there is disclosed an improved start-up procedure wherein the highly selective catalyst is subjected to a heat treatment wherein the catalyst is contacted with a feed comprising oxygen at a temperature above the normal operating temperature of the highly selective catalyst (i.e., above 260° C.). U.S. Pub. Pat. App. 2004/0049061 relates to a method of improving the selectivity of a highly selective catalyst having a low silver density. U.S. Pat. No. 4,874,879 relates to the start-up of an epoxidation process employing a highly selective catalyst wherein the highly selective catalyst is first contacted with a feed containing an organic chloride moderator and ethylene, and optionally a ballast gas, at a temperature below the normal operating temperature of the catalyst. EP-B1-1532125 relates to an improved start-up procedure wherein the highly selective catalyst is first subjected to a pre-soak phase in the presence of a feed containing an organic halide and is then subjected to a stripping phase in the presence of a feed which is free of the organic halide or may comprise the organic halide in a low quantity. The stripping phase is taught to continue for a period of more than 16 hours up to 200 hours. U.S. Pat. App. No. 2009/0281339 relates to the start-up where the organic chloride in the feed is adjusted to a value sufficient to produce EO at a substantially optimum selectivity.

At the end of the start-up period, the chloride level is typically adjusted to find the chloride level which gives the maximum selectivity at the desired EO production rate. The plant then sets the chloride level equal to this so-called "chloride optimum" and begins normal operation of the catalyst, which continues until it is discharged from the reactor. During normal operation of the catalyst, several routine things may happen:

The catalyst will deactivate. In order to maintain a constant production rate, the reaction temperature will be increased as the catalyst deactivates.

The production rate may change, due to feedstock availability, production demands, or economics. To increase the production rate, the reaction temperature will be increased; to decrease the production rate, the reaction temperature will be decreased.

The feed composition may change. Generally, $CO_2$ levels will increase over the life of the catalyst as selectivity drops. Also, ethylene and oxygen levels may be changed due to feedstock issues or to lower temperature near end-of-cycle.

Feed impurities (such as ethane or propane) may fluctuate.

There may be an upset in operation due to such events as equipment failure or unplanned operation changes or deviations from normal operation.

It is well-known (see, e.g., U.S. Pat. No. 7,193,094 and EP 1,458,698) that changes in reaction temperature or hydrocarbon concentration will change the chloride optimum. For example, as the reaction temperature increases or as hydrocarbon levels increase, the chloride level will also need to be increased in order to maintain operation at the maximum selectivity. During routine plant operation, the chloride level is adjusted in one of two methods:

1. The plant utilizes some proprietary mathematical formula which relates chloride level to temperature, composition, etc. This formula is computed periodically and if the chloride level is found to be significantly different than the optimal level (as determined by the formula), then the chloride level is adjusted so that it equals the optimal level.

2. More frequently, the plant routinely checks whether the chloride level is still optimized. This may happen at some fixed frequency or following certain changes in operating conditions, as determined by the plant. Typically, the chloride level is increased or decreased slightly and the plant observes whether the selectivity changed. If it did not change, then they were probably operating at the selectivity maximum, so the chloride level is reset to its original value. If the selectivity did change, then the chloride level is changed in small steps until a selectivity maximum is found, and then the plant continues operation at this new chloride optimum.

Notwithstanding the improvements already achieved, there is a desire to further improve the performance of the silver-containing catalysts in the production of an olefin oxide, a 1,2-diol, a 1,2-diol ether or an alkanolamine.

SUMMARY OF THE INVENTION

The present invention shows that optimum catalyst performance can be achieved faster with the increase in concentration of saturated hydrocarbon co-moderators. Optimum catalyst performance is understood as maximum selectivity. Faster catalyst optimization times consequently lead to a more economical process of ethylene oxide production.

In accordance with this invention, the operation of an epoxidation process using a highly selective catalyst can be improved by utilizing the process steps according to the present invention. In particular, the present invention comprises a process for improving the selectivity of an ethylene epoxidation process employed in a reactor comprising a catalyst bed having a multitude of reactor tubes filled with a high selectivity epoxidation catalyst, said process comprising:

(a) contacting the catalyst bed with a feed comprising ethylene, oxygen, an organic chloride moderator for a period of time $T_1$ to produce ethylene oxide;

(b) subsequently subjecting the high selectivity epoxidation catalyst to a chloride strip over a period of time $T_2$, which comprises:
   (i) reducing the organic chloride added to the feed; and
   (ii) treating the catalyst in order to strip a portion of the chlorides from the surface of the catalyst by adding an effective amount of a saturated hydrocarbon co-moderator; and (c) following the chloride strip, increasing the quantity of organic chloride added to the feed to achieve optimum catalyst performance defined as maximum selectivity or catalyst productivity and reducing the added amount of saturated hydrocarbon co-moderator to maintain optimum catalyst performance.

Step (a) of the present invention comprises the normal operation of the process to produce ethylene oxide according to the design parameters of the plant and process. According to the present invention, it is possible to improve operation and selectivity by inclusion of an intermediate stripping step (b), where the organic chloride is reduced or stopped and the hydrocarbon co-moderator increased (or added) for a period of time, until the chloride level on the catalyst is significantly reduced.

In an optional step following step (c) the various operating conditions may be re-optimized to achieve a new optimum selectivity prior to resuming normal operation. Normal operation would comprise subsequently contacting the catalyst bed with feed comprising ethylene, oxygen, an organic chloride moderator and optionally a saturated $C_{2+}$ hydrocarbon co-moderator.

The organic chloride for use in the present process are typically one or more chloro-hydrocarbons. Preferably, the organic chloride is selected from the group of methyl chloride, ethyl chloride, ethylene dichloride, vinyl chloride or a mixture thereof. The most preferred reaction modifiers are ethyl chloride, vinyl chloride and ethylene dichloride. The $C_{2+}$ saturated hydrocarbon are preferably saturated $C_2$-$C_6$ hydrocarbons (which include ethane, propane, cyclopropane, n-butane and i-butane), more preferably propane and ethane, and most preferably ethane.

The selectivity (to ethylene oxide) indicates the molar amount of ethylene oxide in the reaction product compared with the total molar amount of ethylene converted. By high-selectivity is meant a catalyst with a selectivity greater than 80 molar-%, preferably greater than 85.7 molar-%. One such catalyst is a rhenium containing catalyst, such as that disclosed in U.S. Pat. No. 4,766,105 or US 2009/0281345A1.

$T_1$ refers to the initial period of time following start-up and is defined as the time required to produce 0.1 kiloton of ethylene oxide per cubic meter of catalyst. For the typical range of commercial workrates from 100 to 300 kg/m³/hour, this translates to about 14 to about 42 days. $T_2$ refers to the time period for the chloride strip and should be as short as possible in order to start producing EO at the same or better commercial rates as before the chloride strip. This $T_2$ time period is typically about 2 to 72 hours, more preferably about 4 to about 24 hours.

DETAILED DESCRIPTION OF THE INVENTION

Although the present epoxidation process may be carried out in many ways, it is preferred to carry it out as a gas phase process, i.e. a process in which the feed is contacted in the gas phase with the catalyst which is present as a solid material, typically in a packed bed. Generally the process is carried out as a continuous process. The reactor is typically equipped with heat exchange facilities to heat or cool the catalyst. As used herein, the feed is considered to be the composition which is contacted with the catalyst. As used herein, the catalyst temperature or the temperature of the catalyst bed is deemed to be the temperature approximately half-way through the catalyst bed.

When new catalysts as well as aged catalysts which, due to a plant shut-down, have been subjected to a prolonged shut-in period are utilized in the epoxidation process, it may be useful in some instances to pre-treat these catalysts prior to carrying out the start-up process by passing a sweeping gas over the catalyst at an elevated temperature. The sweeping gas is typically an inert gas, for example nitrogen or argon, or mixtures comprising nitrogen and/or argon. The elevated temperature converts a significant portion of organic nitrogen compounds which may have been used in the manufacture of the catalyst to nitrogen containing gases which are swept up in the gas stream and removed from the catalyst. In addition, any moisture may be removed from the catalyst. Typically, when the catalyst is loaded into the reactor, by utilizing the coolant heater, the temperature of the catalyst is brought up to 200 to 250° C., preferably from 210 to 230° C., and the gas flow is passed over the catalyst. Further details on this pre-treatment may be found in U.S. Pat. No. 4,874,879, which is incorporated herein by reference.

The catalyst is subjected to a start-up process which involves an initial step of contacting the catalyst with a feed comprising ethylene, oxygen, and an organic chloride. For the sake of clarity only, this step of the process will be indicated hereinafter by the term "initial start-up phase". During the initial start-up phase, the catalyst is able to produce ethylene oxide at or near the selectivity experienced after the catalyst has "lined-out" under normal initial operating conditions after the start-up process. In particular, during the initial start-up phase, the selectivity may be within 3 mole-%, more in particular within 2 mole-%, most in particular within 1 mole-% of the optimum selectivity performance under normal initial operating conditions. Suitably, the selectivity may reach and be maintained at more than 86.5 mole-%, in particular at least 87 mole-%, more in particular at least 87.5 mole-% during the initial start-up phase. Since the selectivity of the catalyst quickly increases, there is advantageously additional production of ethylene oxide.

In the initial start-up phase, the catalyst is contacted with organic chloride for a period of time until an increase of at least $1 \times 10^{-5}$ mole-% of vinyl chloride (calculated as the moles of vinyl chloride relative to the total gas mixture) is detected in the reactor outlet or the recycle gas loop. Without wishing to be bound by theory, when using organic chlorides other than vinyl chloride, it is believed that the vinyl chloride detected in the outlet or recycle loop is generated by the reaction of surface adsorbed chloride on the silver present in the catalyst with a $C_2$ hydrocarbon present in the feed. Preferably, the catalyst is contacted with organic chloride for a period of time until an increase of at least $2 \times 10^{-5}$ mole-% of vinyl chloride, in particular at most $1 \times 10^{-4}$ mole-% (calculated as the moles of vinyl chloride relative to the total gas mixture) is detected in the reactor outlet or the recycle gas loop. The quantity of organic chloride contacted with the catalyst may be in the range of from 1 to 12 millimolar (mmolar) equivalent of chloride per kilogram of catalyst. The mmolar equivalent of chloride is determined by multiplying the mmoles of the organic chloride by the number of chloride atoms present in the organic chloride molecule, for example 1 mmole of ethylene dichloride provides 2 mmolar equivalent of chloride. The organic chloride may be fed to the catalyst bed for a period of time ranging from 1 to 15 hours, preferably 2 to 10 hours, more preferably from 2.5 to 8 hours. Suitably, the quantity of the organic chloride contacted with the catalyst may be at most 6 mmolar equivalent/kg catalyst, in particular at most 5.5 mmolar equivalent/kg catalyst, more in particular at most 5 mmolar equivalent/kg catalyst. The quantity of the organic chloride in the feed during the initial start-up phase may be at least $1.5 \times 10^{-4}$ mole-%, in particular at least $2 \times 10^{-4}$ mole-%, calculated as moles of chloride, relative to the total feed. The quantity of the organic chloride during the initial start-up phase may be at most 0.1 mole-%, preferably at most 0.01 mole-%, relative to the total feed. Preferably, the initial start-up feed may comprise the organic chloride in a quantity above the optimum quantity used during the initial period of normal ethylene oxide production.

The feed during the initial start-up phase may also contain additional reaction modifiers which are not organic halides such as nitrate- or nitrite-forming compounds, as described herein.

The feed during the initial start-up phase also contains ethylene. Ethylene may be present in the initial start-up feed in a quantity of at least 10 mole-%, preferably at least 15 mole-%, more preferably at least 20 mole-%, relative to the total feed. Ethylene may be present in the initial start-up feed in a quantity of at most 50 mole-%, preferably at most 45 mole-%, more preferably at most 40 mole-%, relative to the total feed. Preferably, ethylene may be present in the initial start-up feed in the same or substantially the same quantity as utilized during normal ethylene oxide production. This provides an additional advantage in that ethylene concentration does not have to be adjusted between the initial start-up phase and normal ethylene oxide production post start-up making the process more efficient.

The feed during the initial start-up phase also contains oxygen. The oxygen may be present in the initial start-up feed in a quantity of at least 1 mole-%, preferably at least 2 mole-%, more preferably at least 2.5 mole-%, relative to the total feed. The oxygen may be present in the initial start-up feed in a quantity of at most 15 mole-%, preferably at most 10 mole-%, more preferably at most 5 mole-%, relative to the total feed. It may be advantageous to apply a lower oxygen quantity in the initial start-up feed, compared with the feed composition in later stages of the process during normal ethylene oxide production since a lower oxygen quantity in the feed will reduce the oxygen conversion level so that, advantageously, hot spots in the catalyst are better avoided and the process will be more easily controllable.

The feed during the initial start-up phase may also contain carbon dioxide. The carbon dioxide may be present in the initial start-up feed in a quantity of at most 10 mole-%, preferably at most 5 mole-%, relative to the total feed. In an embodiment, the initial start-up phase also contains less than 2 mole-%, preferably less than 1.5 mole percent, more preferably less than 1.2 mole percent, most preferably less than 1 mole percent, in particular at most 0.75 mole percent carbon dioxide, relative to the total feed. In the normal practice of the present invention, the quantity of carbon dioxide present in the reactor feed is at least 0.1 mole percent, or at least 0.2 mole percent, or at least 0.3 mole percent, relative to the total feed. Suitably, the carbon dioxide may be present in the initial start-up feed in the same or substantially the same quantity as utilized during normal ethylene oxide production. The balance of the feed during the initial start-up phase may also contain an inert and/or saturated hydrocarbon.

During the initial start-up phase, the catalyst temperature preferably may be at substantially the same temperature as the normal initial catalyst operating temperature after the epoxidation process has "lined-out" under normal operating conditions after the start-up process. The term "substantially the same temperature" as used herein is meant to include catalyst temperatures within ±5° C. of the normal initial catalyst operating temperature after the epoxidation process has "lined-out" under normal operating conditions after the start-up process. Preferably, the catalyst temperature is less than 250° C., preferably at most 245° C. The catalyst temperature may be at least 200° C., preferably at least 220° C., more preferably at least 230° C. The reactor inlet pressure may be at most 4000 kPa absolute, preferably at most 3500 kPa absolute, more preferably at most 2500 kPa absolute. The reactor inlet pressure is at least 500 kPa absolute. The Gas Hourly Space Velocity or "GHSV", defined hereinafter, may be in the range of from 500 to 10000 Nl (normal liters of gas flow)/l (liters of effective catalyst volume)/hour.

During the initial start-up phase, the catalyst may first be contacted with a feed comprising ethylene and optionally a saturated hydrocarbon, in particular ethane and optionally methane. The organic chloride may then be added to the feed. The oxygen may be added to the feed simultaneously with or shortly after the first addition of the organic chloride to the feed. Within a few minutes of the addition of oxygen, the epoxidation reaction can initiate. Carbon dioxide and additional feed components may be added at any time, preferably simultaneously with or shortly after the first addition of oxygen to the initial start-up feed. As discussed above, during the initial start-up phase, the catalyst is able to produce ethylene oxide at or near the selectivity experienced after the catalyst has "lined-out" under normal initial operating conditions after the start-up process. During the initial start-up phase, the catalyst is operated under conditions such that ethylene oxide is produced at a level that is from 45 to 100% of the targeted production level during normal ethylene oxide production, in particular from 50 to 70%, same basis.

The present epoxidation process may be air-based or oxygen-based, see "Kirk-Othmer Encyclopedia of Chemical Technology", $3^{rd}$ edition, Volume 9, 1980, pp. 445-447. In the air-based process, air or air enriched with oxygen is employed as the source of the oxidizing agent while in the oxygen-based processes, high-purity (at least 95 mole-%) or very high purity (at least 99.5 mole-%) oxygen is employed as the source of the oxidizing agent. Reference may be made to U.S. Pat. No. 6,040,467, incorporated by reference, for further description of oxygen-based processes. Presently most epoxidation plants are oxygen-based and this is a preferred embodiment of the present invention.

In addition to ethylene, oxygen and the organic chloride, the production feed during the normal epoxidation process may contain one or more optional components, such as nitrogen-containing reaction modifiers, carbon dioxide, inert gases and saturated hydrocarbons.

Nitrogen oxides, organic nitro compounds such as nitromethane, nitroethane, and nitropropane, hydrazine, hydroxylamine or ammonia may be employed as reaction modifiers in the epoxidation process. It is frequently considered that under the operating conditions of ethylene epoxidation the nitrogen containing reaction modifiers are precursors of nitrates or nitrites, i.e. they are so-called nitrate- or nitrite-forming compounds. Reference may be made to EP-A-3642 and U.S. Pat. No. 4,822,900, which are incorporated herein by reference, for further description of nitrogen-containing reaction modifiers.

Suitable nitrogen oxides are of the general formula $NO_x$ wherein x is in the range of from 1 to 2.5, and include for example $NO$, $N_2O_3$, $N_2O_4$, and $N_2O_5$. Suitable organic nitrogen compounds are nitro compounds, nitroso compounds, amines, nitrates and nitrites, for example nitromethane, 1-nitropropane or 2-nitropropane.

Carbon dioxide is a by-product in the epoxidation process. However, carbon dioxide generally has an adverse effect on the catalyst activity, and high concentrations of carbon dioxide are therefore typically avoided. A typical epoxidation reactor feed during the normal epoxidation process may contain a quantity of carbon dioxide in the feed of at most 10 mole-%, relative to the total feed, preferably at most 5 mole-%, relative to the total feed. A quantity of carbon dioxide of less than 3 mole-%, preferably less than 2 mole-%, more preferably less than 1 mole-%, relative to the total feed, may be employed. Under commercial operations, a quantity of carbon dioxide of at least 0.1 mole-%, in particular at least 0.2 mole-%, relative to the total feed, may be present in the feed.

The inert gas may be, for example, nitrogen or argon, or a mixture thereof. Suitable saturated hydrocarbons are propane and cyclopropane, and in particular methane and ethane. Saturated hydrocarbons may be added to the feed in order to increase the oxygen flammability limit.

In the normal ethylene oxide production phase, the invention may be practiced by using methods known in the art of epoxidation processes. For further details of such epoxidation methods reference may be made, for example, to U.S. Pat. No. 4,761,394, U.S. Pat. No. 4,766,105, U.S. Pat. No. 6,372,925, U.S. Pat. No. 4,874,879, and U.S. Pat. No. 5,155,242, which are incorporated herein by reference.

In normal ethylene oxide production phase, the process may be carried out using reaction temperatures selected from a wide range. Preferably the reaction temperature is in the range of from 150 to 325° C., more preferably in the range of from 180 to 300° C.

In the normal ethylene oxide production phase, the concentration of the components in the feed may be selected within wide ranges, as described hereinafter.

The quantity of ethylene present in the production feed may be selected within a wide range. The quantity of ethylene present in the feed will be at most 80 mole-%, relative to the total feed. Preferably, it will be in the range of from 0.5 to 70 mole-%, in particular from 1 to 60 mole-%, on the same basis. Preferably, the quantity of ethylene in the production feed is substantially the same as used in the start-up process. If desired, the ethylene concentration may be increased during the lifetime of the catalyst, by which the selectivity may be improved in an operating phase wherein the catalyst has aged, see U.S. Pat. No. 6,372,925 which methods are incorporated herein by reference.

Often present in the feed will be saturated hydrocarbons such as ethane and methane. These saturated hydrocarbons are also termed "co-moderators", since they have an impact on the effect of the chloride "moderators", in that they are effective at removing or "stripping" adsorbed chloride from the surface of the catalyst. The level of ethane is typically 0.05 to 1.5 mole-% of the feed, more typically 0.05 to 0.5 mol-% of the feed, and will depend upon the particular feed stream to the reactor. Such level is monitored, but is not usually controlled during normal operation. However, according to the present invention, the level of ethane co-moderator may be increased in order to assist in the chloride strip.

The quantity of oxygen present in the production feed may be selected within a wide range. However, in practice, oxygen is generally applied in a quantity which avoids the flammable regime. The quantity of oxygen applied will be within the range of from 4 to 15 mole-%, more typically from 5 to 12 mole-% of the total feed.

In order to remain outside the flammable regime, the quantity of oxygen present in the feed may be lowered as the quantity of ethylene is increased. The actual safe operating ranges depend, along with the feed composition, also on the reaction conditions such as the reaction temperature and the pressure.

The organic chlorides are generally effective as a reaction modifier when used in small quantities in the production feed, for example up to 0.1 mole-%, calculated as moles of chloride, relative to the total production feed, for example from $0.01 \times 10^{-4}$ to 0.01 mole-%, calculated as moles of chloride, relative to the total production feed. In particular, it is preferred that the organic chloride may be present in the feed in a quantity of from $1 \times 10^{-4}$ to $50 \times 10^{-4}$ mole-%, in particular from $1.5 \times 10^{-4}$ to $25 \times 10^{-4}$ mole-%, more in particular from $1.75 \times 10^{-4}$ to $20 \times 10^{-4}$ mole-%, calculated as moles of chloride, relative to the total production feed. When nitrogen containing reaction modifiers are applied, they may be present in low quantities in the feed, for example up to 0.1 mole-%, calculated as moles of nitrogen, relative to the total production feed, for example from $0.01 \times 10^{-4}$ to 0.01 mole-%, calculated as moles of nitrogen, relative to the total production feed. In particular, it is preferred that the nitrogen containing reaction modifier may be present in the feed in a quantity of from $0.05 \times 10^{-4}$ to $50 \times 10^{-4}$ mole-%, in particular from 0.2×10$^{-4}$ to 30×10$^{-4}$ mole-%, more in particular from 0.5×10$^{-4}$ to 10×10$^{-4}$ mole-%, calculated as moles of nitrogen, relative to the total production feed.

Inert gases, for example nitrogen or argon, may be present in the production feed in a quantity of 0.5 to 90 mole-%, relative to the total feed. In an air based process, inert gas may be present in the production feed in a quantity of from 30 to 90 mole-%, typically from 40 to 80 mole-%. In an oxygen-based process, inert gas may be present in the production feed in a quantity of from 0.5 to 30 mole-%, typically from 1 to 15 mole-%. If saturated hydrocarbons are present, they may be present in a quantity of up to 80 mole-%, relative to the total production feed, in particular up to 75 mole-%, same basis. Frequently they are present in a quantity of at least 30 mole-%, more frequently at least 40 mole-%, same basis.

In the normal ethylene oxide production phase, the epoxidation process is preferably carried out at a reactor inlet pressure in the range of from 1000 to 3500 kPa. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the epoxidation process is a gas phase process involving a packed catalyst bed, the GHSV is in the range of from 1500 to 10000 Nl/Nl/h. Preferably, the process is carried out at a work rate (productivity) in the range of from 0.5 to 10 kmole ethylene oxide produced per m$^3$ of catalyst per hour, in particular 0.7 to 8 kmole ethylene oxide produced per m$^3$ of catalyst per hour, for example 5 kmole ethylene oxide produced per m$^3$ of catalyst per hour. As used herein, the work rate is the amount of ethylene oxide produced per unit volume of catalyst per hour and the selectivity is the molar quantity of ethylene oxide formed relative to the molar quantity of ethylene converted.

The key to the present invention is to initiate a "chloride strip" of the chlorides following a decline in the selectivity of the catalyst, often attributed to an upset in the process. This step can also be referred to as an "ethane strip", because of the effect of increased ethane on stripping the chlorides. Stripping of the chlorides is typically accomplished by first stopping or significantly reducing the introduction of fresh chloride moderator. The normal level of chloride addition is a function of catalyst, temperature, gas flowrate and catalyst volume. Significantly reducing the amount means to reduce the introduction of fresh chloride moderator into the feed stream to the reactor by at least 25% or 50%, more preferably at least 75% and most preferably by eliminating all the fresh addition of chloride moderator (100% reduction). Then the hydrocarbon co-moderator (preferably the ethane content) is increased in order to strip a portion of the chlorides from the catalyst surface. For use in chloride stripping, the amount of saturated hydrocarbon added to the feed can be increased by about 0.1 to 4 mole-%, preferably about 0.2 to about 2 mole-% based on the feed—this is in addition to the normal level of saturated $C_{2+}$ hydrocarbons already present in the feed stream (if any). In addition, it may also be helpful to increase the reactor temperature by about 1 to about 30° C., preferably by about 2 to about 15° C.

In one embodiment the ethane strip is carried out with no reduction of chloride feed concentration and increase of the hydrocarbon co-moderator (preferably the ethane content) in order to strip a portion of the chlorides from the catalyst surface. For use in chloride stripping, the amount of saturated hydrocarbon added to the feed can be increased by about 0.1 to 4 mole-%, preferably about 0.2 to about 2 mole-% based on the feed—this is in addition to the normal level of saturated $C_{2+}$ hydrocarbons already present in the feed stream (if any).

Following the chloride strip, the chloride is then reintroduced over a relatively short time period until the level reaches approximately the same as prior to the ethane strip. As for the time period for the chloride strip, this should be as short as possible in order to start producing EO at the same or better commercial rates as before the chloride strip. This time period is typically about 2 to 72 hours, more preferably about 4 to about 24 hours.

In a preferred embodiment, the ethane level is reduced by venting or purging of the loop gas stream. This may be accomplished by increasing the venting rate of ethane.

Following the chloride strip, the process may be continued under normal plant conditions. In an optional step the process may be re-optimized following the chloride strip. This may be done by varying the chloride moderator up and down to determine at what level the selectivity is at substantially an optimum. This optimization step is fully described in U.S. Pat. No. 7,193,094 and US Published Application No. 2009/0281339, which disclosures are hereby incorporated by reference.

Following the first "chloride strip", the chloride strip may be repeated later in the run as needed (e.g., if selectivity drops below expectations).

The epoxidation catalyst is a supported catalyst. The carrier may be selected from a wide range of materials. Such carrier materials may be natural or artificial inorganic materials and they include silicon carbide, clays, pumice, zeolites, charcoal, and alkaline earth metal carbonates, such as calcium carbonate. Preferred are refractory carrier materials, such as alumina, magnesia, zirconia, silica, and mixtures thereof. The most preferred carrier material is α-alumina.

The surface area of the carrier may suitably be at least 0.1 m$^2$/g, preferably at least 0.3 m$^2$/g, more preferably at least 0.5 m$^2$/g, and in particular at least 0.6 m$^2$/g, relative to the weight of the carrier; and the surface area may suitably be at most 20 m$^2$/g, preferably at most 10 m$^2$/g, more preferably at most 6 m$^2$/g, and in particular at most 4 m$^2$/g, relative to the weight of the carrier. "Surface area" as used herein is understood to relate to the surface area as determined by the B.E.T. (Brunauer, Emmett and Teller) method as described in Journal of the American Chemical Society 60 (1938) pp. 309-316. High surface area carriers, in particular when they are alpha alumina carriers optionally comprising in addition silica, alkali metal and/or alkaline earth metal components, provide improved performance and stability of operation.

The water absorption of the carrier may suitably be at least 0.2 g/g, preferably at least 0.25 g/g, more preferably at least 0.3 g/g, most preferably at least 0.35 g/g; and the water absorption may suitably be at most 0.85 g/g, preferably at most 0.7 g/g, more preferably at most 0.65 g/g, most preferably at most 0.6 g/g. The water absorption of the carrier may be in the range of from 0.2 to 0.85 g/g, preferably in the range of from 0.25 to 0.7 g/g, more preferably from 0.3 to 0.65 g/g, most preferably from 0.42 to 0.52 g/g. A higher water absorption may be in favor in view of a more efficient deposition of the metal and promoters on the carrier by impregnation. However, at a higher water absorption, the carrier, or the catalyst made therefrom, may have lower crush strength. As used herein, water absorption is deemed to have been measured in accordance with ASTM C20, and water absorption is expressed as the weight of the water that can be absorbed into the pores of the carrier, relative to the weight of the carrier.

A carrier may be washed, to remove soluble residues, before deposition of the catalyst ingredients on the carrier. Additionally, the materials used to form the carrier, including the burnout materials, may be washed to remove soluble residues. Such carriers are described in U.S. Pat. No. 6,368, 998 and WO-A2-2007/095453, which are incorporated herein by reference. On the other hand, unwashed carriers may also be used successfully. Washing of the carrier generally occurs under conditions effective to remove most of the soluble and/or ionizable materials from the carrier.

The washing liquid may be, for example water, aqueous solutions comprising one or more salts, or aqueous organic diluents. Suitable salts for inclusion in an aqueous solution may include, for example ammonium salts. Suitable ammonium salts may include, for example ammonium nitrate, ammonium oxalate, ammonium fluoride, and ammonium carboxylates, such as ammonium acetate, ammonium citrate, ammonium hydrogencitrate, ammonium formate, ammonium lactate, and ammonium tartrate. Suitable salts may also include other types of nitrates such as alkali metal nitrates, for example lithium nitrate, potassium nitrate and cesium nitrate. Suitable quantities of total salt present in the aqueous solution may be at least 0.001% w, in particular at least 0.005% w, more in particular at least 0.01% w and at most 10% w, in particular at most 1% w, for example 0.03% w. Suitable organic diluents which may or may not be included are, for example, one or more of methanol, ethanol, propanol, isopropanol, tetrahydrofuran, ethylene glycol, ethylene glycol dimethyl ether, diethylene glycol dimethyl ether, dimethylformamide, acetone, or methyl ethyl ketone.

The preparation of the silver catalyst is known in the art and the known methods are applicable to the preparation of the catalyst which may be used in the practice of the present invention. Methods of depositing silver on the carrier include impregnating the carrier or carrier bodies with a silver compound containing cationic silver and/or complexed silver and performing a reduction to form metallic silver particles. For further description of such methods, reference may be made to U.S. Pat. No. 5,380,697, U.S. Pat. No. 5,739,075, U.S. Pat. No. 4,766,105, and U.S. Pat. No. 6,368,998, which are incorporated herein by reference. Suitably, silver dispersions, for example silver sols, may be used to deposit silver on the carrier.

The reduction of cationic silver to metallic silver may be accomplished during a step in which the catalyst is dried, so that the reduction as such does not require a separate process step. This may be the case if the silver containing impregnation solution comprises a reducing agent, for example, an oxalate, a lactate or formaldehyde.

Appreciable catalytic activity is obtained by employing a silver content of the catalyst of at least 10 g/kg, relative to the weight of the catalyst. Preferably, the catalyst comprises silver in a quantity of from 10 to 500 g/kg, more preferably from 50 to 450 g/kg, for example 105 g/kg, or 120 g/kg, or 170 g/kg, or 190 g/kg, or 250 g/kg, or 350 g/kg. As used herein, unless otherwise specified, the weight of the catalyst is deemed to be the total weight of the catalyst including the weight of the carrier and catalytic components.

In an embodiment, the catalyst employs a silver content of the catalyst of at least 150 g/kg, relative to the weight of the catalyst. Preferably, the catalyst comprises silver in a quantity of from 150 to 500 g/kg, more preferably from 170 to 450 g/kg, for example 190 g/kg, or 250 g/kg, or 350 g/kg.

The catalyst for use in the present invention additionally comprises a rhenium promoter component. The form in which the rhenium promoter may be deposited onto the carrier is not material to the invention. For example, the rhenium promoter may suitably be provided as an oxide or as an oxyanion, for example, as a rhenate or perrhenate, in salt or acid form.

The rhenium promoter may be present in a quantity of at least 0.01 mmole/kg, preferably at least 0.1 mmole/kg, more preferably at least 0.5 mmole/kg, most preferably at least 1 mmole/kg, in particular at least 1.25 mmole/kg, more in particular at least 1.5 mmole/kg, calculated as the total quantity of the element relative to the weight of the catalyst. The rhenium promoter may be present in a quantity of at most 500 mmole/kg, preferably at most 50 mmole/kg, more preferably at most 10 mmole/kg, calculated as the total quantity of the element relative to the weight of the catalyst.

In an embodiment, the rhenium promoter is present in a quantity of at least 1.75 mmole/kg, preferably at least 2 mmole/kg, calculated as the total quantity of the element relative to the weight of the catalyst. The rhenium promoter may be present in a quantity of at most 15 mmole/kg, preferably at most 10 mmole/kg, more preferably at most 8 mmole/kg, calculated as the total quantity of the element relative to the weight of the catalyst.

In an embodiment, the catalyst may further comprise a potassium promoter deposited on the carrier. The potassium promoter may be deposited in a quantity of at least 0.5 mmole/kg, preferably at least 1 mmole/kg, more preferably at least 1.5 mmole/kg, most preferably at least 1.75 mmole/kg, calculated as the total quantity of the potassium element deposited relative to the weight of the catalyst. The potassium promoter may be deposited in a quantity of at most 20 mmole/kg, preferably at most 15 mmole/kg, more preferably at most 10 mmole/kg, most preferably at most 5 mmole/kg, on the same basis. The potassium promoter may be deposited in a quantity in the range of from 0.5 to 20 mmole/kg, preferably from 1 to 15 mmole/kg, more preferably from 1.5 to 7.5 mmole/kg, most preferably from 1.75 to 5 mmole/kg, on the same basis. A catalyst prepared in accordance with the present invention can exhibit an improvement in selectivity, activity, and/or stability of the catalyst especially when operated under conditions where the reaction feed contains low levels of carbon dioxide.

The catalyst for use in the present invention may additionally comprise a rhenium co-promoter. The rhenium co-promoter may be selected from tungsten, molybdenum, chromium, sulfur, phosphorus, boron, and mixtures thereof.

The rhenium co-promoter may be present in a total quantity of at least 0.1 mmole/kg, more typically at least 0.25 mmole/kg, and preferably at least 0.5 mmole/kg, calculated as the element (i.e. the total of tungsten, chromium, molybdenum, sulfur, phosphorus and/or boron), relative to the weight of the catalyst. The rhenium co-promoter may be present in a total quantity of at most 40 mmole/kg, preferably at most 10 mmole/kg, more preferably at most 5 mmole/kg, on the same basis. The form in which the rhenium co-promoter may be deposited on the carrier is not material to the invention. For example, it may suitably be provided as an oxide or as an oxyanion, for example, as a sulfate, borate or molybdate, in salt or acid form.

In an embodiment, the catalyst contains the rhenium promoter and tungsten in a molar ratio of the rhenium promoter to tungsten of greater than 2, more preferably at least 2.5, most preferably at least 3. The molar ratio of the rhenium promoter to tungsten may be at most 20, preferably at most 15, more preferably at most 10.

In an embodiment, the catalyst comprises the rhenium promoter and additionally a first co-promoter component and a second co-promoter component. The first co-promoter may be selected from sulfur, phosphorus, boron, and mixtures thereof. It is particularly preferred that the first co-promoter comprises, as an element, sulfur. The second co-promoter component may be selected from tungsten, molybdenum, chromium, and mixtures thereof. It is particularly preferred that the second co-promoter component comprises, as an element, tungsten and/or molybdenum, in particular tungsten. The form in which the first co-promoter and second co-promoter components may be deposited onto the carrier is not material to the invention. For example, the first co-promoter and second co-promoter components may suitably be provided as an oxide or as an oxyanion, for example, as a tungstate, molybdate, or sulfate, in salt or acid form.

In this embodiment, the first co-promoter may be present in a total quantity of at least 0.2 mmole/kg, preferably at least 0.3 mmole/kg, more preferably at least 0.5 mmole/kg, most preferably at least 1 mmole/kg, in particular at least 1.5 mmole/kg, more in particular at least 2 mmole/kg, calculated as the total quantity of the element (i.e., the total of sulfur, phosphorus, and/or boron) relative to the weight of the catalyst. The first co-promoter may be present in a total quantity of at most 50 mmole/kg, preferably at most 40 mmole/kg, more preferably at most 30 mmole/kg, most preferably at most 20 mmole/kg, in particular at most 10 mmole/kg, more in particular at most 6 mmole/kg, calculated as the total quantity of the element relative to the weight of the catalyst.

In this embodiment, the second co-promoter component may be present in a total quantity of at least 0.1 mmole/kg, preferably at least 0.15 mmole/kg, more preferably at least 0.2 mmole/kg, most preferably at least 0.25 mmole/kg, in particular at least 0.3 mmole/kg, more in particular at least 0.4 mmole/kg, calculated as the total quantity of the element (i.e., the total of tungsten, molybdenum, and/or chromium) relative to the weight of the catalyst. The second co-promoter may be present in a total quantity of at most 40 mmole/kg, preferably at most 20 mmole/kg, more preferably at most 10 mmole/kg, most preferably at most 5 mmole/kg, calculated as the total quantity of the element relative to the weight of the catalyst.

In an embodiment, the molar ratio of the first co-promoter to the second co-promoter may be greater than 1. In this embodiment, the molar ratio of the first co-promoter to the second co-promoter may preferably be at least 1.25, more preferably at least 1.5, most preferably at least 2, in particular at least 2.5. The molar ratio of the first co-promoter to the second co-promoter may be at most 20, preferably at most 15, more preferably at most 10.

In an embodiment, the molar ratio of the rhenium promoter to the second co-promoter may be greater than 1. In this embodiment, the molar ratio of the rhenium promoter to the second co-promoter may preferably be at least 1.25, more preferably at least 1.5. The molar ratio of the rhenium promoter to the second co-promoter may be at most 20, preferably at most 15, more preferably at most 10.

In an embodiment, the catalyst comprises the rhenium promoter in a quantity of greater than 1 mmole/kg, relative to the weight of the catalyst, and the total quantity of the first co-promoter and the second co-promoter deposited on the carrier may be at most 12 mmole/kg, calculated as the total quantity of the elements (i.e., the total of sulfur, phosphorous, boron, tungsten, molybdenum and/or chromium) relative to the weight of the catalyst. In this embodiment, the total quantity of the first co-promoter and the second co-promoter may preferably be at most 10 mmole/kg, more preferably at most 8 mmole/kg of catalyst. In this embodiment, the total quantity of the first co-promoter and the second co-promoter may preferably be at least 0.1 mmole/kg, more preferably at least 0.5 mmole/kg, most preferably at least 1 mmole/kg of the catalyst.

The catalyst may preferably further comprise a further element deposited on the carrier. Eligible further elements may be one or more of nitrogen, fluorine, alkali metals, alkaline earth metals, titanium, hafnium, zirconium, vanadium, thallium, thorium, tantalum, niobium, gallium and germanium and mixtures thereof. Preferably, the alkali metals are selected from lithium, sodium and/or cesium. Preferably, the alkaline earth metals are selected from calcium, magnesium and barium. Preferably, the further element may be present in the catalyst in a total quantity of from 0.01 to 500 mmole/kg, more preferably from 0.5 to 100 mmole/kg, calculated as the total quantity of the element relative to the weight of the catalyst. The further element may be provided in any form. For example, salts or hydroxides of an alkali metal or an alkaline earth metal are suitable. For example, lithium compounds may be lithium hydroxide or lithium nitrate.

In an embodiment, the catalyst may comprise cesium as a further element in a quantity of more than 1.0 mmole/kg, in particular at least 2.0 mmole/kg, more in particular at least 3.0 mmole/kg, calculated as the total quantity of the element relative to the weight of the catalyst. In this embodiment, the catalyst may comprise cesium in a quantity of at most 20 mmole/kg, in particular at most 15 mmole/kg, calculated as the total quantity of the element relative to the weight of the catalyst As used herein, unless otherwise specified, the quantity of alkali metal present in the catalyst and the quantity of water leachable components present in the carrier are deemed to be the quantity insofar as it can be extracted from the catalyst or carrier with de-ionized water at 100° C. The extraction method involves extracting a 10-gram sample of the catalyst or carrier three times by heating it in 20 ml portions of de-ionized water for 5 minutes at 100° C. and determining in the combined extracts the relevant metals by using a known method, for example atomic absorption spectroscopy.

As used herein, unless otherwise specified, the quantity of alkaline earth metal present in the catalyst and the quantity of acid leachable components present in the carrier are deemed to be the quantity insofar as it can be extracted from the catalyst or carrier with 10% w nitric acid in de-ionized water at 100° C. The extraction method involves extracting a 10-gram sample of the catalyst or carrier by boiling it with a 100 ml portion of 10% w nitric acid for 30 minutes (1 atm., i.e. 101.3 kPa) and determining in the combined extracts the relevant metals by using a known method, for example atomic absorption spectroscopy. Reference is made to U.S. Pat. No. 5,801,259, which is incorporated herein by reference.

Ethylene oxide produced may be recovered from the product mix by using methods known in the art, for example by absorbing ethylene oxide from a reactor outlet stream in water and optionally recovering ethylene oxide from the aqueous solution by distillation. At least a portion of the aqueous solution containing ethylene oxide may be applied in a subsequent process for converting ethylene oxide into a 1,2-diol, a 1,2-diol ether, a 1,2-carbonate, or an alkanolamine, in particular ethylene glycol, ethylene glycol ethers, ethylene carbonate, or alkanol amines.

Ethylene oxide produced in the epoxidation process may be converted into a 1,2-diol, a 1,2-diol ether, a 1,2-carbonate, or an alkanolamine. As this invention leads to a more attractive process for the production of ethylene oxide, it concurrently leads to a more attractive process which comprises producing ethylene oxide in accordance with the invention and the subsequent use of the obtained ethylene oxide in the manufacture of the 1,2-diol, 1,2-diol ether, 1,2-carbonate, and/or alkanolamine.

The conversion into the 1,2-diol (i.e., ethylene glycol) or the 1,2-diol ether (i.e., ethylene glycol ethers) may comprise, for example, reacting ethylene oxide with water, suitably using an acidic or a basic catalyst. For example, for making predominantly the 1,2-diol and less 1,2-diol ether, ethylene oxide may be reacted with a ten fold molar excess of water, in a liquid phase reaction in presence of an acid catalyst, e.g. 0.5-1.0% w sulfuric acid, based on the total reaction mixture, at 50-70° C. at 1 bar absolute, or in a gas phase reaction at 130-240° C. and 20-40 bar absolute, preferably in the absence of a catalyst. The presence of such a large quantity of water may favor the selective formation of 1,2-diol and may function as a sink for the reaction exotherm, helping control the reaction temperature. If the proportion of water is lowered, the proportion of 1,2-diol ethers in the reaction mixture is increased. Alternative 1,2-diol ethers may be prepared by converting ethylene oxide with an alcohol, in particular a primary alcohol, such as methanol or ethanol, by replacing at least a portion of the water by the alcohol.

Ethylene oxide may be converted into the corresponding 1,2-carbonate by reacting ethylene oxide with carbon dioxide. If desired, ethylene glycol may be prepared by subsequently reacting the 1,2-carbonate with water or an alcohol to form the glycol. For applicable methods, reference is made to U.S. Pat. No. 6,080,897, which is incorporated herein by reference.

The conversion into the alkanolamine may comprise, for example, reacting ethylene oxide with ammonia. Anhydrous ammonia is typically used to favor the production of monoalkanolamine. For methods applicable in the conversion of ethylene oxide into the alkanolamine, reference may be made to, for example U.S. Pat. No. 4,845,296, which is incorporated herein by reference.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The 1,2-carbonates may be used as a diluent, in particular as a solvent. The alkanolamine may be used, for example, in the treating ("sweetening") of natural gas.

Example 1

In Example 1 an experiment was run to show the effect of increasing the ethane co-moderator level to affect a chloride strip. In this experiment a rhenium containing high selectivity catalyst according to US 2009/0281345A1 was loaded into a pilot plant reactor. The catalyst was operated under a variety of conditions over a period of several weeks after which the conditions were changed to the following: 30 mole-% ethylene, 8 mole-% oxygen, 3 mole-% carbon dioxide with the balance nitrogen and a reactor inlet pressure of 241 psig. The coolant temperature was set at 220° C. and the ethyl chloride concentration was set at 4 ppm. During several hours of operation the catalyst selectivity reached maximum and then slowly decreased resulting in a non-optimum catalyst performance. When the catalyst selectivity reached 85%, a chloride strip was conducted. In the first chloride strip, the chloride addition to the reactor was cut to zero, the reactor temperature was kept at 220° C., and the catalyst performance was monitored. The same experiment was performed a second time, but in addition to the chloride being cut to zero, 0.6 mole-% ethane was added to the feed gas. The results from these two experiments are shown in FIG. 1.

Figure 1:
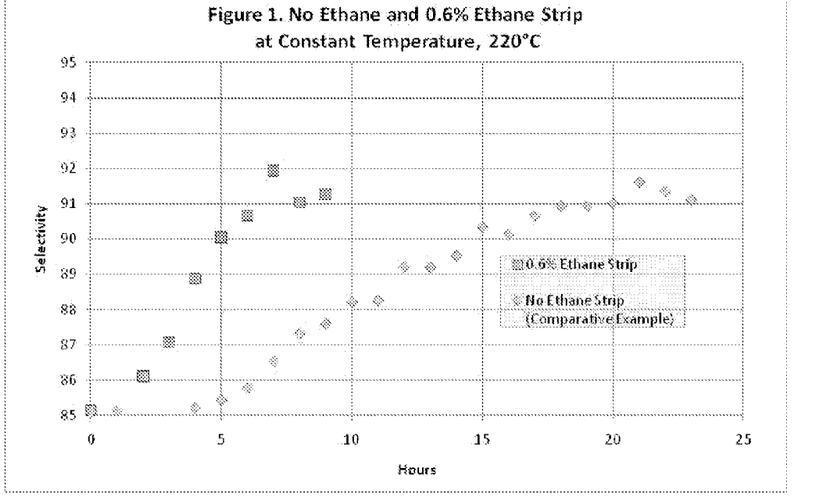
FIG. 1 is a graph showing selectivity over time for both a chloride strip using ethane and a comparative example with no ethane in the feed.

It is evident from FIG. 1 that in the absence of ethane it took 21 hours to recover catalyst performance and reach maximum selectivity, while in the presence of added ethane it took only 7 hours to reach maximum selectivity. Thus, the increase in ethane resulted in a shorter time that the catalyst was operated in a non-optimized state, bringing significant economic benefits to the catalyst operator.

What is claimed is:

1. A process for improving the selectivity of an ethylene epoxidation process employed in a reactor, said process comprising:
   (a) contacting an epoxidation catalyst comprising silver and rhenium with a feed comprising ethylene, oxygen, and an organic chloride for a period of time $T_1$ sufficient to produce at least 0.1 kilotons of ethylene oxide per cubic meter of epoxidation catalyst;
   (b) subsequent to step (a) and over a period of time $T_2$,
      (i) reducing the quantity of organic chloride added to the feed by at least 25% and
      (ii) adding a saturated hydrocarbon co-moderator to the feed in an amount of at least 0.1 to 4 mole-%, based on the feed; and
   (c) subsequent to step (b), increasing the quantity of organic chloride added to the feed and terminating the addition of the saturated hydrocarbon co-moderator to the feed.

2. The process of claim 1 wherein said organic chloride is selected from the group consisting of methyl chloride, ethyl chloride, ethylene dichloride, vinyl chloride and mixtures thereof.

3. The process of claim 2 wherein said saturated hydrocarbon co-moderator is a $C_{2+}$ saturated hydrocarbon selected from the group consisting of ethane, propane, n-butane, i-butane, cyclopropane and mixtures thereof.

4. The process of claim 3 wherein said saturated hydrocarbon co-moderator is ethane.

5. The process of claim 3 wherein the quantity of organic chloride present in the feed in step (a) is in the range of from $0.01 \times 10^{-4}$ to 0.01 mole-%, calculated as moles of chloride, relative to the total feed.

6. The process of claim 5 wherein in step (b), the quantity of organic chloride added to the feed is reduced by at least 75%.

7. The process of claim 1 wherein in step (b), the reactor temperature is increased by about 1 to about 30° C.

8. The process of claim 1 wherein in step (b), the reactor temperature is increased by about 2 to about 15° C.

9. The process of claim 1 wherein the saturated hydrocarbon co-moderator comprises ethane, and the amount of ethane added to the feed during step (b) is about 0.1 to about 2 mole-% based on the feed.

10. The process of claim 1 wherein the saturated hydrocarbon co-moderator comprises ethane, and the amount of ethane added to the feed during step (b) is about 0.2 to about 1 mole-% based on the feed.

11. The process of claim 7 wherein the saturated hydrocarbon co-moderator comprises ethane, and the amount of ethane added to the feed during step (b) is about 0.1 to about 2 mole-% based on the feed.

12. The process of claim 8 wherein the saturated hydrocarbon co-moderator comprises ethane, and the amount of ethane added to the feed during step (b) is about 0.2 to about 1 mole-% based on the feed.

13. The process of claim 1 wherein $T_2$ is about 2 hours to about 72 hours.

14. The process of claim 1 wherein $T_2$ is about 4 to 24 hours.

15. The process of claim 1 wherein
rhenium is present in the epoxidation catalyst in an amount greater than 1 mmole/kg, relative to the weight of the catalyst; and wherein the epoxidation catalyst further comprises
   (a) a first co-promoter selected from the group consisting of sulfur, phosphorus, boron, and mixtures thereof; and (b) a second co-promoter selected from the group consisting of tungsten, molybdenum, chromium, and mixtures thereof.

16. The process of claim 15 wherein the total quantity of the first co-promoter and the second co-promoter is at most 10 mmole/kg, relative to the weight of the catalyst; and said wherein the epoxidation catalyst further comprises a carrier having a monomodal, bimodal or multimodal pore size distribution, with a maximum pore diameter range of 0.01-200 µm, a specific surface area of 0.03-10 m$^2$/g, a pore volume of 0.2-0.7 cm$^3$/g, wherein the median pore diameter of said carrier is 0.1-100 µm and has a water absorption of 10-80%.

17. The process of claim 1 wherein the feed further comprises $CO_2$ in a quantity that is less than 2%.

18. The process of claim 1 further comprising reacting at least a portion of the ethylene oxide with at least one selected from the group consisting of water, an alcohol, carbon dioxide and an amine to form, respectively, a 1,2-diol, a 1,2-diol ether, a 1,2-carbonate, or an alkanolamine.

19. A process for improving the selectivity of an ethylene epoxidation process employed in a reactor, said process comprising:
(a) contacting an epoxidation catalyst comprising silver and rhenium with a feed comprising ethylene, oxygen, and an organic chloride for a period of time sufficient to produce at least 0.1 kilotons of ethylene oxide per cubic meter of epoxidation catalyst;
(b) subsequent to step (a) and over a period of about 2 to 72 hours, (i) reducing the quantity of organic chloride added to the feed by at least 25% and (ii) adding a saturated hydrocarbon co-moderator to the feed in an amount of at least 0.1 to 4 mole-%, based on the feed; and
(c) subsequent to step (b), increasing the quantity of organic chloride added to the feed and terminating the addition of the saturated hydrocarbon co-moderator to the feed.

\* \* \* \* \*